United States Patent [19]
Dreier

[11] Patent Number: 5,531,730
[45] Date of Patent: *Jul. 2, 1996

[54] ABSORBENT ARTICLE HAVING A POCKET CUFF

[75] Inventor: Kimberly A. Dreier, Cincinnati, Ohio

[73] Assignee: The Procter & Gamble Company, Cincinnati, Ohio

[ * ] Notice: The term of this patent shall not extend beyond the expiration date of Pat. No. 5,397,318.

[21] Appl. No.: 441,145

[22] Filed: May 15, 1995

Related U.S. Application Data

[63] Continuation of Ser. No. 302,569, Sep. 8, 1994, which is a continuation-in-part of Ser. No. 75,205, Jun. 10, 1993, Pat. No. 5,397,318.

[51] Int. Cl.$^6$ .................................................. A61F 13/15
[52] U.S. Cl. ............................... 604/385.2; 604/385.1
[58] Field of Search .................... 604/629, 385.1–386, 604/389–391, 393–402

[56] References Cited

U.S. PATENT DOCUMENTS

| | | |
|---|---|---|
| 3,930,501 | 1/1976 | Schaar . |
| 3,951,150 | 4/1976 | Schaar . |
| 3,990,450 | 11/1976 | Schaar . |
| 4,662,877 | 5/1987 | Williams . |
| 4,738,677 | 4/1988 | Foreman . |
| 4,743,246 | 5/1988 | Lawson . |
| 4,808,177 | 2/1989 | Desmarais et al. ............ 604/385.1 |
| 4,816,025 | 3/1989 | Foreman ........................ 604/385.2 |
| 4,892,536 | 1/1990 | Desmarais et al. ............ 604/385.2 |
| 4,895,568 | 1/1990 | Enloe ............................. 604/385.2 |
| 4,938,755 | 7/1990 | Foreman ........................ 604/385.2 |
| 4,990,147 | 2/1991 | Freeland ........................ 604/385.2 |
| 5,026,364 | 6/1991 | Robertson ...................... 604/385.1 |
| 5,037,416 | 8/1991 | Allen et al. .................... 604/385.1 |
| 5,085,654 | 2/1992 | Buell ............................. 604/370 |
| 5,087,255 | 2/1992 | Sims .............................. 604/385.1 |
| 5,151,092 | 9/1992 | Buell et al. .................... 604/385.2 |
| 5,171,236 | 12/1992 | Dreier et al. .................. 604/369 |
| 5,176,672 | 1/1993 | Bruemmer et al. ........... 604/385.1 |
| 5,187,817 | 2/1993 | Zolner .......................... 2/400 |
| 5,207,663 | 5/1993 | McQueen ..................... 604/385.1 |
| 5,246,431 | 9/1993 | Minitils ......................... 604/385.2 |
| 5,304,159 | 4/1994 | Tanji et al. ................... 604/385.2 |
| 5,304,160 | 4/1994 | Igaue et al. ................... 604/385.2 |
| 5,344,516 | 9/1994 | Tanji et al. ................... 156/164 |
| 5,397,318 | 3/1995 | Drier ............................. 604/385.2 |

FOREIGN PATENT DOCUMENTS

| | | |
|---|---|---|
| 0149999 | 7/1985 | European Pat. Off. ........... 604/386 |
| 0433951A2 | 6/1991 | European Pat. Off. . |
| 0486006A2 | 5/1992 | European Pat. Off. . |
| 3-218751 | 9/1991 | Japan . |
| 4297256 | 10/1992 | Japan ............................... 604/385.1 |
| 4354945 | 12/1992 | Japan ............................... 604/394 |
| 2159693 | 12/1985 | United Kingdom . |
| 2174591 | 11/1986 | United Kingdom . |
| 2265550 | 10/1993 | United Kingdom . |
| 2261944 | 11/1993 | United Kingdom ........... 604/385.2 |
| 8902228 | 3/1989 | WIPO .............................. 604/385.1 |
| 8022271 | 12/1992 | WIPO .............................. 604/385.2 |

*Primary Examiner*—David H. Willse
*Assistant Examiner*—Mark O. Polutta
*Attorney, Agent, or Firm*—Gerry S. Gressel; Larry L. Huston; E. Kelly Linman

[57] ABSTRACT

A disposable diaper having a waist pocket cuff is disclosed. The pocket cuff has an open edge having an apex. The open edge extends between ends joined to the distal edges of barrier cuffs. The open edge is elastically biased to form the open edge apex along the longitudinal centerline of the disposable diaper.

14 Claims, 6 Drawing Sheets

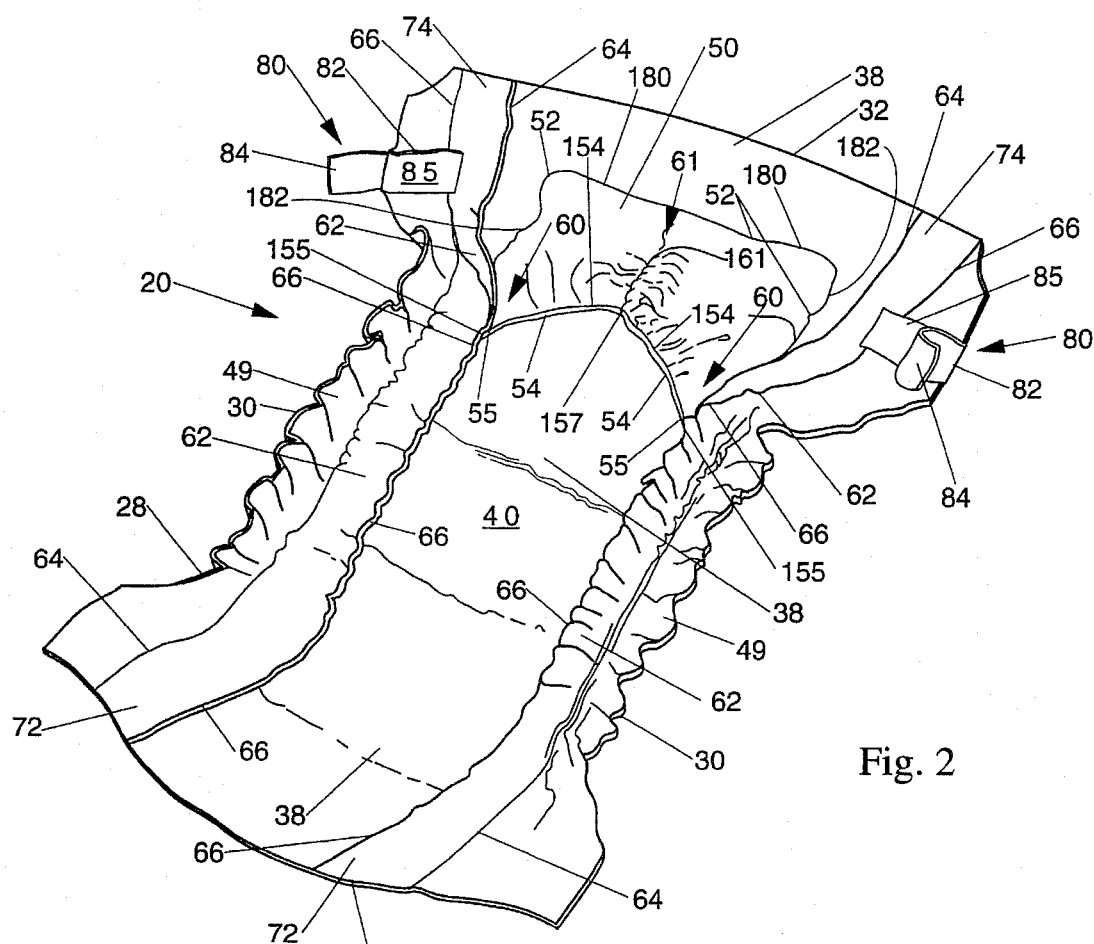
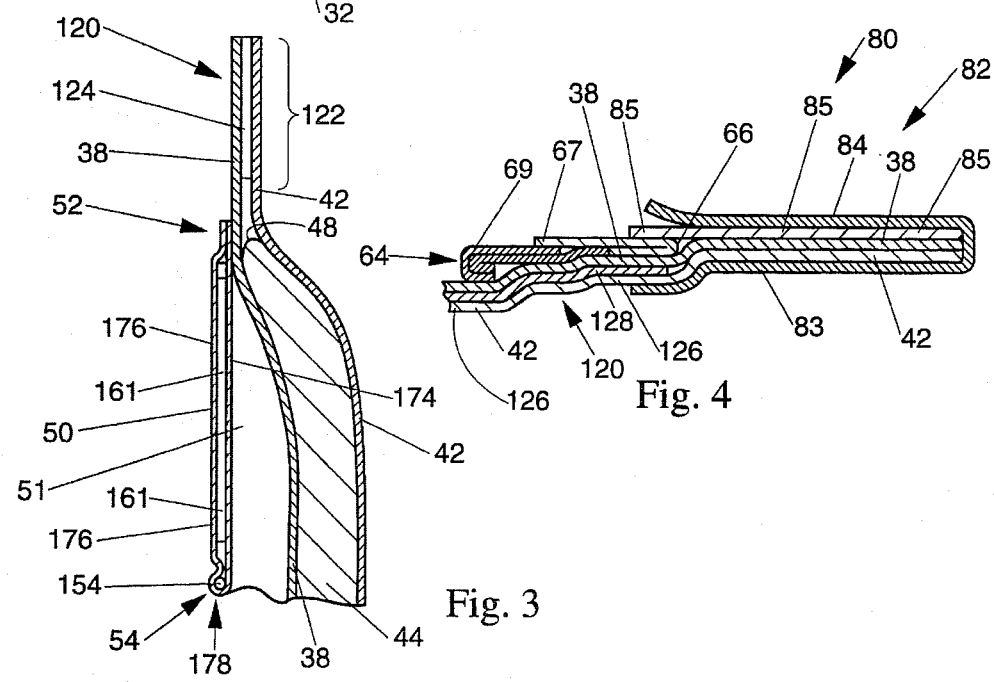
Fig. 2
Fig. 3
Fig. 4

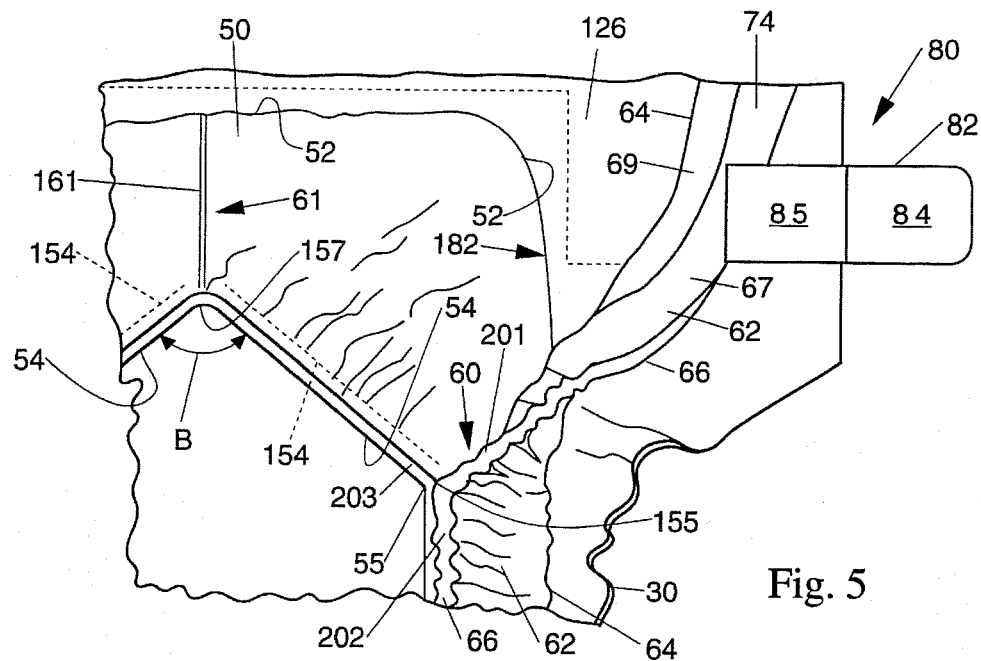
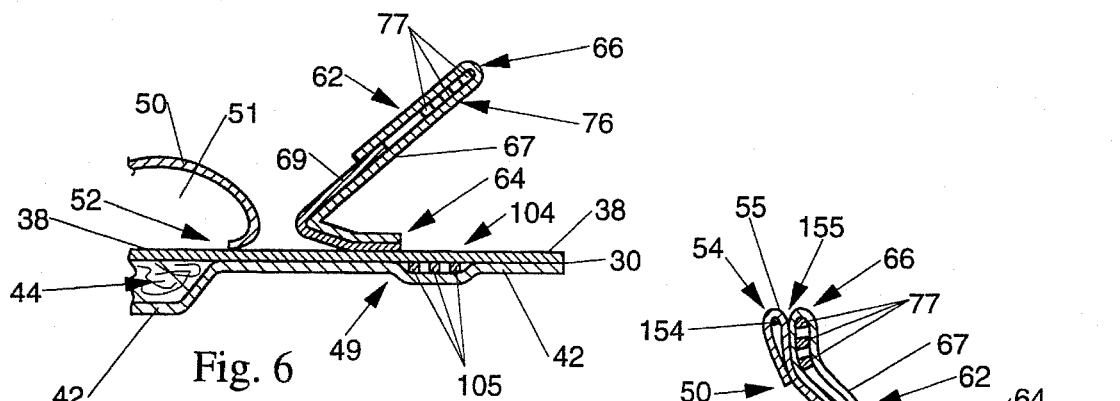
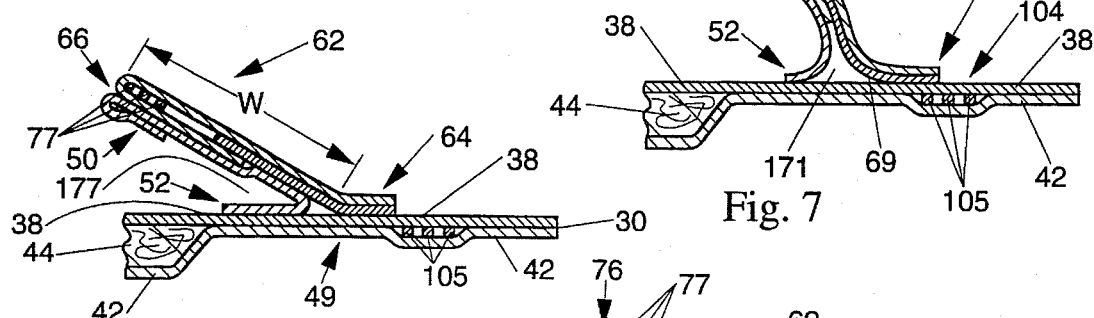
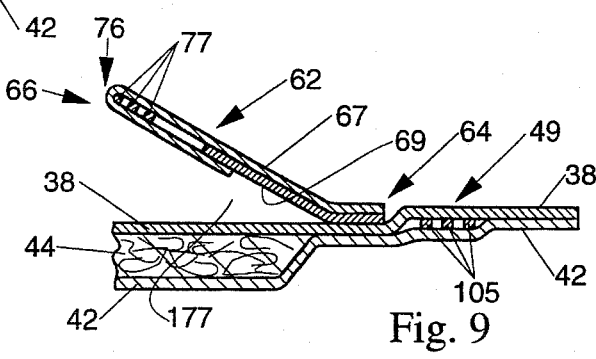

ABSORBENT ARTICLE HAVING A POCKET CUFF

This is a continuation of application Ser. No. 08/302,569, filed on Sep. 8, 1994, which is a continuation-in-part of Ser. No. 08/075,205 filed on Jun. 10, 1993 now U.S. Pat. No. 5,397,318.

FIELD OF THE INVENTION

The present invention relates to absorbent articles such as disposable diapers, and more particularly, to absorbent articles having a fecal containment pocket cuff having an open edge with an apex.

BACKGROUND OF THE INVENTION

The major function of absorbent articles such as disposable diapers and incontinence briefs or undergarments is to absorb and contain body exudates. Such articles are thus intended to prevent body exudates from soiling, wetting, or otherwise contaminating clothing or other articles, such as bedding, that come in contact with the wearer. The most common mode of failure for such products occurs when body exudates leak out of the gaps between the article and the wearer's leg or waist. Fecal material that is not absorbed by the absorbent article can work its way past the gaps in the article in the legs or waist of the wearer.

Contemporary disposable diapers have a topsheet, a backsheet, an absorbent core, and elasticized leg or gasket cuffs generally formed from an elastic member enclosed between portions of the topsheet and backsheet which extend beyond the edges of the absorbent core. These elasticized leg or gasket cuffs present a barrier between the edge of the diaper and the wearer's contacting clothing, and in addition, provide a gasketing action about the legs of the wearer to maintain a seal about the leg and minimize gapping.

Disposable diapers may also be provided with barrier cuffs which inhibit fecal material or gushes of urine or liquids from soiling the wearer's clothing. The barrier cuffs restrain the free flow of this material to hold such material within the diaper. U.S. Pat. No. 4,743,246 issued May 10, 1988, to Lawson discloses an absorbent article having gasket and barrier cuffs.

Disposable diapers having an opening formed in a topsheet are disclosed in the following references: GB Application 2,265,550A published Oct. 6, 1993 in the name of Tanji et al.; U.S. Pat. No. 5,176,672 issued Jan. 5, 1993 to Bruemmer et al.; U.S. Pat. No. 5,304,159 issued Apr. 19, 1994 to Tanji et al.; and U.S. Pat. No. 5,304,160 issued Apr. 19, 1994 to Igaue et al.

Disposable diapers may also have pockets or waistcaps for reducing the leakage of body exudates from the diaper waist region. Examples of such diapers are disclosed in U.S. Pat. No. 4,738,677 issued Apr. 19, 1988, to Foreman, and U.S. Pat. No. 5,026,364 issued Jun. 25, 1991, to Robertson.

Despite the effectiveness of such pockets in containing waste material, it has been found that liquid and solid material can leak past the pocket and soil the wearer's clothing, under certain conditions. For instance, forces exerted on the pocket when the diaper is worn may cause the pocket to be pressed against the diaper topsheet, so that the pocket is not open to receive fecal matter. Moreover, the shape and construction of the pocket may promote gaps between the pocket cuff and the wearer's buttocks, thereby providing a leakage path for fecal matter in the absorbent article waist region.

Therefore, it is an object of the present invention to provide an absorbent article which has improved containment characteristics.

It is an additional object of the present invention to provide an absorbent article having a pocket cuff which acts as a restraint against the leakage of body exudates from the waist region of an absorbent article.

It is also an object of the present invention to provide an absorbent article having a pocket cuff with an open edge having an apex.

It is a still further object of the present invention to provide an absorbent article having a pocket cuff extending intermediate barrier cuffs.

These and other objects of the invention will be more readily apparent when considered in reference to the following description and when taken in connection with the accompanying drawings.

SUMMARY OF THE INVENTION

In accordance with the present invention, a disposable absorbent article, such as a diaper, is provided with a liquid pervious topsheet; a liquid impervious backsheet joined to the topsheet; an absorbent core positioned intermediate the topsheet and the backsheet; and a pocket cuff overlying portion of the topsheet. The pocket cuff has an open edge with an apex, the open edge extending between open edge ends. The pocket cuff can also have a closed edge, and side edges extending longitudinally rearward from the open edge ends.

The diaper includes a pair of barrier cuffs, each barrier cuff positioned adjacent a longitudinal edge of the diaper. Spacing means operatively associated with each barrier cuff aid in spacing the distal edge of each barrier cuff apart from the topsheet. The open edge of the pocket cuff extends intermediate the barrier leg cuffs and the spacing means. The spacing means can comprise elastic members which elastically gather at least a portion of each side edge of the pocket cuff.

The pocket cuff open edge can be elastically biased to form the open edge apex. In one embodiment the pocket cuff open edge is elastically extensible intermediate the apex and each of the pocket cuff open edge ends, and can comprise an elastic element extending intermediate the open edge ends. A portion of the pocket cuff longitudinally rearward of the open edge and substantially aligned with the longitudinal centerline of the disposable absorbent article can be joined to an underlying portion of the disposable absorbent article, such as the topsheet, to elastically extend the open edge of the pocket cuff and to position the apex longitudinally rearward of the open edge ends. The closed edge of the pocket cuff can include a central closed edge portion and generally forward extending closed edge portions. The central closed edge portion is substantially aligned with the longitudinal centerline of the disposable absorbent article and disposed intermediate and longitudinally rearward of the generally forward extending closed edge portions. The closed edge can be curved to be convex rearward.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

FIG. 2 is a perspective view of the disposable diaper embodiment of FIG. 1.

FIG. 3 is a fragmentary sectional view taken along section line 3—3 of FIG. 1.

FIG. 4 is a fragmentary sectional view taken along section line 4—4 of FIG. 1.

FIG. 5 is a fragmentary top plan view of the disposable diaper embodiment of FIG. 1 enlarged to show the juncture of the pocket cuff with an inflected barrier leg cuff.

FIG. 6 is a fragmentary instant sectional view taken along line 6—6 of FIG. 1.

FIG. 7 is a fragmentary instant sectional view taken along line 7—7 of FIG. 1.

FIG. 8 is a fragmentary instant sectional view taken along line 8—8 of FIG. 1.

FIG. 9 is a fragmentary instant sectional view taken along line 9—9 of FIG. 1.

DETAILED DESCRIPTION OF THE INVENTION

As used herein, the term "absorbent article" refers to articles which absorb and contain body exudates and more specifically refers to articles which are placed against or in proximity to the body of the wearer to absorb and contain the various exudates discharged from the body. Absorbent articles are typically differentiated by whether they are reusable or disposable. The term "disposable absorbent article" refers to articles which are intended to be discarded after a single use (i.e., they are not intended to be laundered or otherwise restored or reused). The absorbent articles of the present invention are preferably disposable absorbent articles. The absorbent articles may be further defined by whether they are "unitary" such that they do not require separate manipulative parts or whether they comprise an element of a diaper system such as a separate holder and liner. The absorbent articles of the present invention are preferably unitary. As used herein, the term "diaper" refers to a garment generally worn by infants and incontinent persons that is worn about the lower torso of the wearer. It should be understood, however, that the present invention is also applicable to other disposable absorbent articles such as incontinence briefs or undergarments, disposable training pants, diaper holders, sanitary napkins, and the like.

Figure 1:
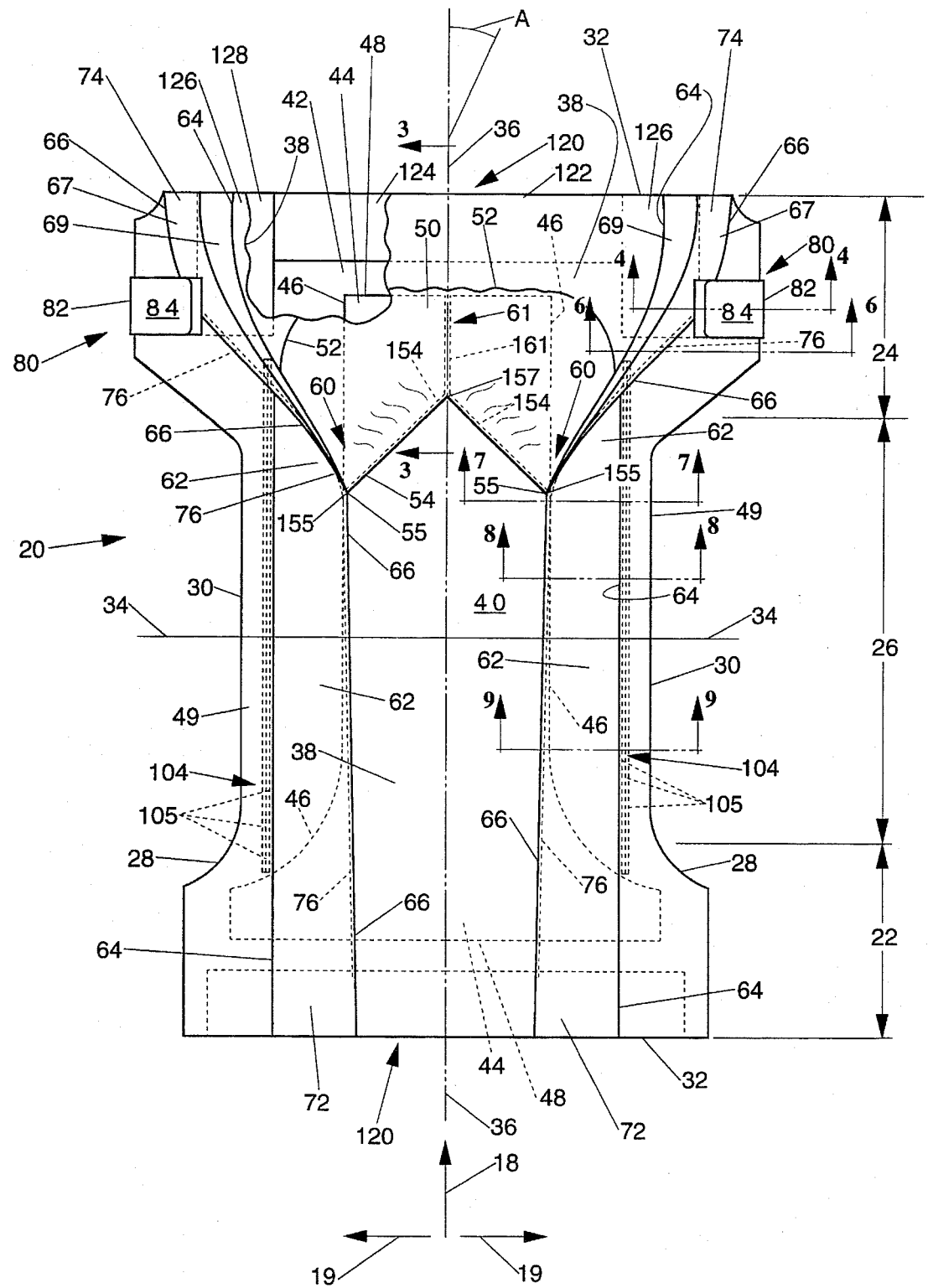
FIG. 1 is a top plan view of a disposable diaper having portions cut-away to reveal underlying structure.

FIG. 1 is a plan view of a diaper 20 with portions of the structure being cut away to more clearly show the construction of the diaper 20, and with the portion of the diaper 20 which contacts the wearer facing the viewer. FIG. 2 is a perspective view of the diaper 20 with the portion of the diaper 20 which contacts the wearer facing the viewer. The diaper 20 shown in FIGS. 1 and 2 has a first front waist region 22, a second rear waist region 24, a crotch region 26 disposed between the front and rear waist regions 22, 24, and a periphery 28 which is defined by longitudinal edges 30 and front and rear end edges 32. The diaper 20 additionally has a lateral centerline 34 and a longitudinal centerline 36.

FIG. 3 is a fragmentary sectional view taken along section line 3—3 in FIG. 1. Referring to FIGS. 1, 2 and 3, the diaper 20 comprises a liquid pervious topsheet 38, the liquid receiving surface of the diaper 20 being generally defined by the topsheet 38 and being designated 40; a liquid impervious backsheet 42 joined to the topsheet 38; and an absorbent core 44 positioned intermediate the topsheet 38 and the backsheet 42. The absorbent core 44 has side edges 46 and front and rear waist edges 48. The diaper 20 also includes a marginal side flap 49 extending laterally outward from each side edge 46 of the absorbent core 44 in at least the crotch region 26.

The diaper 20 further includes a pocket cuff 50 overlying a portion of the topsheet 38. The pocket cuff 50 has a closed edge 52 which can be juxtaposed with the rear waist region 24, and an open edge 54 extending between laterally spaced apart open edge ends 55. In the embodiment shown in FIG. 1, the open edge ends 55 are positioned intermediate lateral centerline 34 and the rear end edge 32. The open edge 54 has an apex 157 positioned substantially on the longitudinal centerline 36, and can include an elastic member 154. The pocket cuff 50 and the topsheet 38 together define a fecal containment pocket space 51 therebetween, as shown in FIG. 3.

In the embodiment of FIG. 1, the diaper 20 also includes pocket cuff biasing means 60 for exerting a longitudinally rearward force component on the pocket cuff 50. Pocket cuff biasing means 60 shapes the open edge 54 and biases the open edge 54 away from the lateral centerline 34 and apart from topsheet 38. The pocket cuff biasing means 60 can also exert a laterally outward force component on the pocket cuff 50. "Longitudinally rearward" refers to a direction which is generally parallel to the longitudinal centerline 36 and which is directed as shown by arrow 18 in FIG. 1. "Laterally outward" refers to a direction which is generally parallel to the lateral centerline 34 and which is directed away from the longitudinal centerline 36 as shown by arrows 19 in FIG. 1.

The pocket cuff biasing means 60 can comprise a portion of barrier cuffs 62 joined to side flaps 49. The pocket cuff open edge 54 extends between open edge ends 55. Each end 55 is joined to a respective barrier cuff 62. In FIG. 1, a portion of each barrier cuff 62 extends longitudinally rearward and laterally outward from a respective open edge end 55. A portion of each barrier cuff 62 also extends longitudinally forward from a respective open edge end 55.

The diaper 20 can also include a longitudinally oriented biasing means 61, such as an elastic member 161, for exerting a longitudinal force component on the pocket cuff 50 intermediate the pocket cuff open edge ends 55. A "longitudinally oriented biasing means" refers to a biasing means which exerts a force oriented to form an included angle A (FIG. 1) with the longitudinal centerline 36 of no more than 45 degrees.

The diaper 20 preferably includes a "dual tension fastening system" as disclosed in U.S. Pat. No. 5,151,092, issued to Buell et al. on Sep. 29, 1992. A dual tension fastening system can include fastening means 80 for securing the diaper on the wearer, such as a pair of tape tab fasteners 82 disposed in the rear waist region 24. Suitable fastening means 80 include but are not limited to adhesive fasteners and mechanical fasteners. U.S. Pat. No. 5,151,092 is incorporated herein by reference to show the construction of such a dual tension fastening system.

In the embodiment shown in FIG. 1, the pocket cuff biasing means 60 can be operatively associated with the fastening means 80. By "operatively associated" it is meant that pocket biasing means 60 and the fastening means 80 work together such that forces used to secure the diaper 20 to the wearer are transmitted from the fastening means 80 through the pocket cuff biasing means 60 to shape the pocket cuff open edge 54. The forces transmitted through the pocket cuff biasing means 60 can bias the pocket cuff open edge 54 away from the topsheet 38 and away from the lateral centerline 34.

Examining the individual components of the diaper 20 in more detail, FIG. 1 shows an embodiment of the diaper 20 in which the backsheet 42 has length and width dimensions generally larger than those of the absorbent core 44. The backsheet 42 extends beyond the edges of the absorbent core 44 to thereby form the periphery 28 of the diaper 20. The periphery 28 defines the outer perimeter or, in other words, the edges of the diaper 20. The periphery 28 comprises the longitudinal edges 30 and the end edges 32 in the front and rear waist regions 22 and 24. As shown in FIG. 1, the topsheet 38 is generally coterminous with the backsheet 42 along at least the end edges 32 and the longitudinal edges 30. U.S. Pat. No. 3,860,003, issued to Buell on Jan. 14, 1975 and above referenced U.S. Pat. No. 5,151,092 are incorporated herein by reference for the purpose of showing such diaper configurations. In an alternative embodiment, the topsheet 38 may have length or width dimensions generally smaller than those of the backsheet 42.

The diaper 20 has a first waist region 22 and a second waist region 24 extending, respectively, from the end edges 32 of the diaper periphery 28 toward the lateral centerline 34 of the diaper 20 a distance up to about ⅓, preferably from about ⅛ to about ¼, of the length of the diaper 20. The waist regions 22 and 24 generally comprise those portions of the diaper 20 which, when worn, encircle the waist of the wearer. The crotch region 26 is that portion of the diaper 20 positioned between the first waist region 22 and the second waist region 24, and comprises that portion of the diaper 20 which, when worn, is positioned between the legs of the wearer and covers the lower torso of the wearer.

Referring to FIGS. 1 and 3, the absorbent core 44 is disposed between the topsheet 38 and the backsheet 42. The topsheet 38 and the backsheet 42 extend beyond the side edge 46 of the absorbent core 44 to form the side flap 49. Each side flap 49 can include a gasket cuff 104 comprising one or more elastic strands 105 (three strands shown in FIG. 1) positioned outboard of the barrier cuff 62. U.S. Pat. No. 4,695,278 issued to Lawson on Sep. 22, 1987, and above referenced U.S. Pat. No. 3,860,003 are incorporated herein by reference to show the construction of such a gasket cuff 104.

The topsheet 38 and backsheet 42 also can extend beyond the waist edge 48 of the absorbent core 44 in front and rear waist regions 22 and 24, as shown in FIGS. 1 and 3. Front and rear waist regions 22 and 24 can include a waist region elastic feature 120 for providing lateral expansion of at least a portion of the front and rear waist regions 22 and 24. Rear waist region elastic feature 120 can include an elasticized waistband 122 extending laterally intermediate a pair of elasticized side panels 126.

The elasticized waistband 122 can comprise a portion of the topsheet 38, a portion of the backsheet 42, and a bilaminate material 124 positioned between the topsheet 38 and the backsheet 42. Referring to FIGS. 1 and 4, elasticized side panels 126 can comprise a portion of the topsheet 38, a portion of the backsheet 42, and an elastic side panel member 128 positioned between the topsheet 38 and the backsheet 42. Above referenced U.S. Pat. No. 5,151,092 is incorporated herein by reference to show the construction of an elastic feature 120, including elasticized side panels 126 and elasticized waistband 122. Alternatively, the rear waist region elastic feature 120 can comprise an elasticized waistband constructed in accordance with U.S. Pat. No. 4,515,595 issued to Kievit et al. on May 7, 1985, which patent is incorporated herein by reference.

FIG. 1 shows the diaper 20 in its flat-out, uncontracted state (i.e., with all the elastic induced contraction in the barrier cuffs 62, gasket cuffs 104, and waist elastic features 120 pulled out). The elastic members 154 and 161 can maintain at least some elastic contraction when the diaper is in its flat-out, uncontracted state. FIG. 2 shows the diaper 20 contracted, with at least some elastic induced contraction in the barrier cuffs 62, the gasket cuffs 104, and waist elastic features 120.

The absorbent core 44 may be any means which is generally compressible, conformable, non-irritating to the wearer's skin, and capable of absorbing and retaining liquids and certain body exudates. The absorbent core 44 may be manufactured in a wide variety of sizes and shapes including, but not limited to, rectangular, hourglass, asymmetric, and T-shaped. The absorbent core 44 can be manufactured from a wide variety of liquid absorbent materials commonly used in disposable diapers and other absorbent articles, such as comminuted wood pulp which is generally referred to as airfelt.

Examples of other suitable absorbent materials include creped cellulose wadding, absorbent foams, absorbent sponges, super absorbent polymers, absorbent gelling materials, or any equivalent materials or combination of materials. The total absorbent capacity of the absorbent core 44 should, however, be compatible with the design exudate loading in the intended use of the diaper 20. Further, the size and absorbent capacity of the absorbent core 44 may be varied to accommodate wearers ranging from infants through adults.

The absorbent core 44 may comprise a layer of absorbent material comprising hydrophilic fibers and particles of absorbent gelling material (hydrogel) such as the absorbent structure described in U.S. Pat. No. 4,610,678 issued to Weisman et al. on Sep. 9, 1986. U.S. Pat. No. 4,673,402 issued to Weisman et al. on Jun. 16, 1987, and U.S. Pat. No. 4,888,321 issued Dec. 19, 1989, to Angstadt also describe absorbent structures that are useful in the present invention. The absorbent core 44 can be the commercially successful absorbent member described in U.S. Pat. No. 4,834,735 issued May 30, 1989, to Alemany et al. The four above mentioned patents are incorporated herein by reference for the purpose of showing suitable constructions for absorbent core 44.

The backsheet 42 is positioned adjacent the absorbent core 44 and can be secured thereto by core attachment means (not shown) such as those well known in the art. For example, the backsheet 42 may be secured to the absorbent core 44 by a uniform continuous layer of adhesive, a patterned layer of adhesive, or an array of separate lines or spots of adhesive. Adhesives which have been found to be satisfactory are manufactured by Century Adhesives, Inc. of Columbus, Ohio and marketed under the trade name Century 5227; and by H. B. Fuller Company of St. Paul, Minn. and marketed as HL-1258. The core attachment means can comprise an open pattern network of filaments of adhesive as is shown in U.S. Pat. No. 4,573,986 issued to Minetola et al. on Mar. 4, 1986, and which is incorporated herein by reference. An exemplary attachment means of an open pattern network of filaments comprises several lines of adhesive filaments swirled into a spiral pattern such as is illustrated in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference for the purpose of showing suitable attachment means.

The backsheet 42 is impervious to liquids and is preferably manufactured from a thin plastic film, although other flexible liquid impervious materials may also be used. The term "flexible" refers to materials which are compliant and which will readily conform to the contours of the human body. The backsheet 42 prevents the exudates absorbed and contained in the absorbent core 44 from wetting articles which contact the diaper 20 such as bedsheets and undergarments. The backsheet 42 may comprise a woven or nonwoven material, polymer films such as thermoplastic films of polyethylene or polypropylene, or composite materials such as film coated nonwoven material. Preferably, the backsheet 42 is a thermoplastic film having a thickness of from about 0.012 mm (0.5 mil) to about 0.051 cm (2.0 mils).

At least a portion of the backsheet 42 can be subjected to mechanical stretching to form elasticized side panels 126 and to pre-strain a portion of the backsheet coinciding with waist region elastic feature 120, as is more fully described in above referenced U.S. Pat. No. 5,151,092. Preferred polymer films for use as the backsheet 42 contain a high content of linear low density polyethylene.

Suitable materials for the backsheet include blends comprised of about 45–90% linear low density polyethylene and about 10–55% polypropylene. Exemplary films for use as the backsheet 42 of the present invention are manufactured by Tredegar Industries Inc. of Terre Haute, Ind. under the designation RR8220 blend for blown films and RR5475 blend for cast films.

The backsheet 42 can be embossed, such as to a caliper of about 0.127 mm (5.5 mils), and/or matte finished to provide a more clothlike appearance. Further, the backsheet 42 may permit vapors to escape from the absorbent core 44 while still preventing exudates from passing through the backsheet 42.

The size of the backsheet 42 is dictated by the size of the absorbent core 44 and the exact diaper design selected. In one embodiment, the backsheet 42 has a modified hourglass shape extending beyond the absorbent core 44 a minimum distance of at least about 1.3 cm to about 2.5 cm (about 0.5 to about 1.0 inch) around the entire diaper periphery 28.

The topsheet 38 is joined to the absorbent core 44 and the backsheet 42 by attachments means (not shown) such as those well known in the art. Suitable attachment means are described above with respect to joining the backsheet 42 to the absorbent core 44. As used herein, the term "joined" encompasses configurations whereby an element is directly secured to the other element by affixing the element directly to the other element, as well as configurations whereby the element is indirectly secured to the other element by affixing the element to intermediate members which in turn are affixed to the other element. In one embodiment the topsheet 38 and the backsheet 42 are joined directly to each other in at least a portion of the periphery 28 of the diaper 20, and are indirectly joined together by directly joining the topsheet 38 and the backsheet 42 to the absorbent core 44.

The topsheet 38 is compliant, soft feeling, and non-irritating to the wearer's skin. Further, the topsheet 38 is liquid pervious permitting liquids to readily penetrate through its thickness. A suitable topsheet may be manufactured from a wide range of materials, such as porous foams, reticulated foams, apertured plastic film, natural fibers (e.g., wood or cotton fibers), synthetic fibers (e.g., polyester or polypropylene fibers) or from a combination of natural and synthetic fibers. Preferably, it is made of a hydrophobic material to isolate the wearer's skin from liquids in the absorbent core 44. At least a portion of topsheet 38 may be subjected to mechanical stretching to form the elasticized side panels 126, as is disclosed in above referenced U.S. Pat. No. 5,151,092.

There are a number of manufacturing techniques which may be used to manufacture the topsheet 38. For example, the topsheet 38 may be a nonwoven web of fibers. When the top sheet 38 comprises a nonwoven web, the web may be spunbonded, carded, wet-laid, meltblown, hydroentangled, or the like. A suitable topsheet 38 can be carded and thermally bonded by means well known to those skilled in the fabric art. A suitable topsheet 38 comprises staple length polypropylene fibers having a length of at least about 15.9 mm (0.625 inch) and has a basis weight from about 18 to about 25 grams per square meter. A suitable topsheet material is manufactured by Veratec, Inc., a Division of International Paper Company, of Walpole, Mass., under the designation P-8.

Referring to FIGS. 1, 4, and 9, each barrier cuff 62 has a proximal edge 64, a distal edge 66, a first barrier cuff end 72 positioned in the front waist region 22, and a second barrier cuff end 74 positioned in the rear waist region 24. The barrier cuff 62 further comprises a spacing means 76 operatively associated with the barrier cuff 62 for spacing the distal edge 66 apart from the topsheet 38. The spacing means 76 can comprise one or more elastic members 77, as shown in FIG. 9. Barrier cuff 62 can comprise a laminate of a nonwoven material layer 67 secured to a liquid impermeable polyethylene film layer 69. Layers 67 and 69 can be secured to each other by any method as is known in the art.

The barrier cuff 62 is preferably formed by joining portions of a separate barrier cuff member to the diaper 20 adjacent the longitudinal edge 30. The proximal edge 64 of the barrier cuff 62 is formed by joining a segment of the barrier cuff member to the diaper 20 by a seal means (not shown) so as to form a seal along the proximal edge 64, and to present a barrier to liquids wicking past the barrier cuffs 62. The seal means can comprise any of several securement means known in the art such as ultrasonic bonds, heat/pressure bonds, or seals using a variety of bonding patterns, or adhesives or glues. A suitable seal means comprising one or more lines of hot melt adhesive is disclosed in U.S. Pat. No. 5,087,255 issued Feb. 11, 1992, to Sims, which patent is incorporated herein by reference.

The proximal edge 64 is preferably joined to the side flap 49 to be positioned laterally inward of the gasket cuff 104 in the crotch region 26. The proximal edge 64 can be joined to the topsheet 38. Alternatively, if the topsheet 38 does not extend laterally outward of the barrier cuff 62, the proximal edge 64 can be joined to the backsheet 42.

As shown in FIG. 9, the distal edge 66 is formed by folding the barrier cuff 62 back upon itself and securing it to another segment of the barrier cuff 62 to form a hem. The spacing means 76, preferably the three elastic members 77 shown in FIG. 9, is enclosed in the hem.

The elastic members 77 are operatively associated with the barrier cuff 62 by an attachment means (not shown). The attachment means preferably secures the elastic members 77 to the barrier cuff 62 in an elastically contractible condition. The elastic members 77 contract or gather the distal edge 66 of the barrier cuff 62, so that the distal edge 66 is spaced away from the topsheet 38, as shown in FIGS. 6–9.

The elastic members 77 can be made from a number of suitable materials including elastomeric films, polyurethane films, Lycra, elastomeric foams, and formed elastic scrim. A suitable elastic member 77 includes an elastic strand having a cross section of 0.18 mm by 1.5 mm and made from natural rubber, such as is available from Easthampton Rubber Company of Stewart, Va. as L-1900 Rubber Compound. Other suitable elastic members include elastic tapes such as those sold by the Fulflex Company of Middletown, R.I. under the name Fulflex 9411. A suitable elastic attachment means for securing elastic members 77 to barrier cuff 62 can include an adhesive, such as a hot melt adhesive marketed by Findley Adhesives of Elmgrove, Wis. as Findley Adhesive 581.

A more detailed description of the manner in which elastic members 77 can be secured to barrier cuffs 62 in an elastically contractible manner can be found in the following patents which are incorporated herein by reference: U.S. Pat. No. 3,860,003 issued to Buell on Jan. 26, 1974; U.S. Pat. No. 4,081,301 issued to Buell on Mar. 28, 1978; and U.S. Pat. No. 4,253,461 issued to Strickland et al. on Mar. 3, 1981.

The distal edge 66 is secured to the diaper 20 at the first and second barrier cuff ends 72 and 74 in the front and rear waist regions 22 and 24, respectively. The distal edge 66 can be secured to an underlying element of the diaper 20, such as the topsheet 38. Alternatively, the distal edge 66 can be secured to the backsheet 42 if the topsheet 38 does not extend fully into the front or rear waist regions 22 and 24. The distal edge 66 can be secured to the underlying element by any of several securement means known in the art such as ultrasonic bonds, heat/pressure bonds, or seals using a variety of bonding patterns, or adhesives or glues. A suitable securement means comprising one or more beads of hot melt adhesive is disclosed in above referenced U.S. Pat. No. 5,087,255, which patent is incorporated herein by reference.

In the embodiment of FIGS. 1 and 2, the barrier cuff 62 is secured at the first and second barrier cuff ends 72 and 74 so as to have an inflected configuration. By an "inflected" configuration it is meant that the distal edge 66 is secured to extend laterally inward of the proximal edge 64 at the first barrier cuff end 72, and that the distal edge 66 is secured to extend laterally outward of the proximal edge 64 at the second barrier cuff end 74. The barrier cuff 62 is thereby turned, or "flipped out" as the barrier cuff 62 extends from the front waist region 22 to the rear waist region 24. An example of an inflected barrier cuff is disclosed in above referenced U.S. Pat. No. 5,087,255, which patent is incorporated herein by reference for the purpose of showing an inflected barrier leg cuff construction. In an alternative embodiment described below, the barrier cuffs 62 can have a non-inflected configuration.

The distal edge 66 is preferably not directly secured to underlying elements of the diaper 20, such as the topsheet 38 or backsheet 42, in the crotch region 26. The distal edge 66 can therefore be spaced away from the liquid-receiving surface 40 of the topsheet 38 by the elastic gathering action of the elastic members 77. However, the distal edge 66 can be joined to the pocket cuff 50 in the crotch region 26, as will be described in more detail below.

The pocket cuff 50 preferably comprises a material that is compliant, soft, and non-irritating to the wearer's skin. The pocket cuff 50 can be formed from a material that is liquid pervious or liquid impervious. A suitable pocket cuff 50 may be made from a wide range of materials, such as apertured plastic films, or woven or nonwoven webs of natural fibers (e.g., wood or cotton fibers) or synthetic fibers (e.g., polyester polypropylene, or rayon fibers), or composites of polyolefinic films and nonwovens. Optionally, the pocket cuff 50 may formed from an elastomeric web of material. The pocket cuff 50 can be hydrophobic to isolate the wearer's skin from liquids contained in the pocket space 51 formed between the topsheet 38 and the pocket cuff 50. A number of techniques may be used to manufacture the pocket cuff 50. For example, the pocket 50 may be a nonwoven web of fibers spunbonded, carded, wet laid, meltblown, hydroentangled, or the like. A suitable pocket cuff 50 comprises a web of staple length polypropylene fibers. Suitable materials from which the pocket cuff 50 can be made are manufactured by Veratec, Inc., a Division of International Paper Company, of Walpole, Mass., under the designations P-8, P-9, or P-11.

Referring to FIGS. 1 and 5, the open edge 54 of pocket cuff 50 can be elastically extensible, and can comprise an elastic member 154 which extends intermediate pocket cuff open edge ends 55. In the embodiment shown in FIGS. 1 and 5, the pocket cuff 50 preferably also comprises a longitudinally oriented biasing means 61. The longitudinally oriented biasing means 61 can comprise an elastic member 161 extending intermediate the forward edge 54 and closed edge 52 of pocket cuff 50. The elastic member 161 is preferably substantially aligned with longitudinal centerline 36 and is preferably equidistantly spaced from the open edge ends 55.

Elastic members 154 and 161 can comprise one or more elastic elements and can comprise a wide variety of materials as are well known in the art including natural or synthetic rubber, elastomeric films, elastic tapes, polyurethane films, Lycra, elastomeric foams, and formed elastic scrim. Generally, materials used to form the elastic members 77 can also be used to form elastic members 154 and 161. One suitable material for forming elastic members 154 and 161 comprises elastic strands having a cross-section of 0.18 mm by 1.5 mm and made from natural rubber as available from Easthampton Rubber Company of Stewart, Va. under the name L-1900 Rubber Compound. Another suitable material for forming elastic members 154 and 161 comprises a double sided adhesive elastic film such as Findley Film No. 198-338 having a thickness of about 0.25 mm and a width of about 12.7 mm available from Findley Adhesives of Elmgrove, Wis. Another suitable material for forming members 154 and 161 is Fulflex Ultraflex synthetic rubber manufactured by the Fulflex Company as Spec. No. 65325, 9EX29, 0.007×5/64.

The elastic member 154 is preferably secured to the pocket cuff 50 in an elastically contractible manner so that in an unrestrained configuration the elastic member 154 gathers the open edge 54. The elastic element 161 is also preferably secured to the pocket cuff 50 in an elastically contractible manner so that the elastic member 161 exerts a longitudinally rearward force component on the open edge 54. The longitudinal rearward force component gathers the pocket cuff 50 to space the open edge 54 apart from the top sheet 38.

Figure 10:
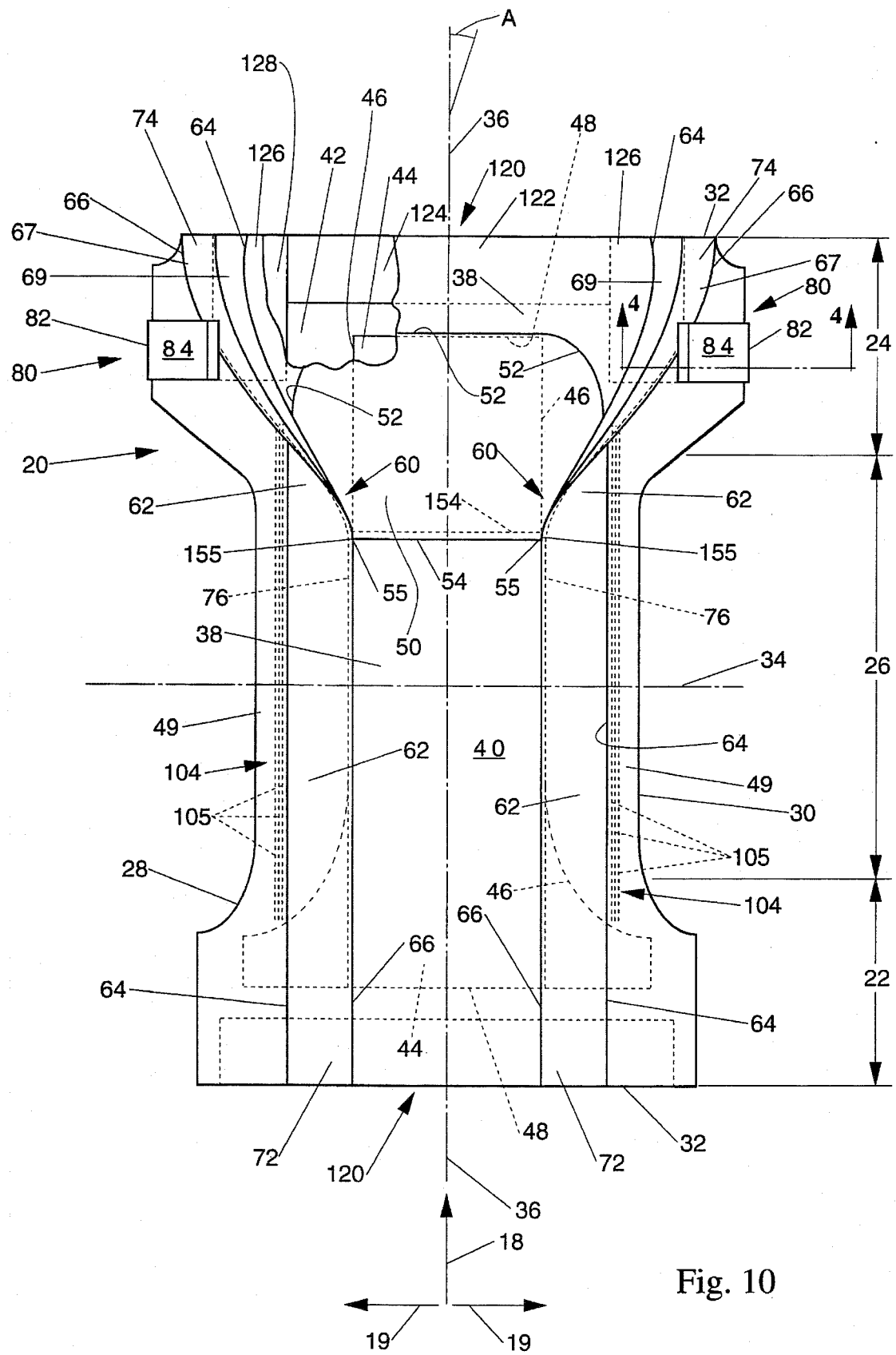
FIG. 10 is a top plan view of a disposable diaper having a pocket cuff with a substantially laterally extending open edge.

In the embodiment shown in FIGS. 1 and 5, the longitudinal rearward force component provided by the elastic member 161 also preferably shapes the open edge 54 to form an apex 157 substantially positioned on longitudinal centerline 36 to be generally aligned with the wearer's gluteal groove, and spaced approximately equidistant from open edge ends 55. The apex 157 is disposed longitudinally rearward of an imaginary lateral line passing through the open edge ends 55. The portions of the open edge 54 extending from each open edge end 55 to the apex 157 are gathered by elastic member 154. The open edge 54 can thereby form a seal or gasket with the wearer's buttocks on each side of the wearer's gluteal groove. FIG. 10 shows a disposable diaper having a pocket cuff open edge 54 which does not include an apex 157.

The apex 157 forms one vertex of an imaginary triangle. The imaginary triangle has vertices at apex 157 and at open edge ends 55. The open edge 54 comprises two sides of the imaginary triangle, and forms an included angle B (FIG. 5) at apex 157.

The open edge 54 can also be shaped to extend longitudinally rearward of the open edge ends 55 by varying the stiffness of the elastic element 154 as a function of position along open edge 54. A portion of the open edge 54 can be curved to extend rearward of the open edge ends 55 if the stiffness, or spring rate, of the elastic member 154 has a maximum value at the center of the open edge 54, and a lower stiffness value adjacent the open edge ends 55. Such a stiffness variation can be obtained in a number of ways. For example, the elastic member 154 can comprise two elastic elements centered on the open edge 54 and having different lengths.

Referring to FIG. 3, the pocket cuff 50 can be formed from a sheet of material, such as a nonwoven, having two sheet halves 174 and 176. The elastic element 154 can be secured along a length of the sheet half 174 adjacent to sheet half 176 in an elastically contractible manner, such as by stretching the elastic member 154 and securing the stretched elastic member 154 to the sheet half 174 with an adhesive. The elastic member 161 can be secured along the width of sheet half 174 in an elastically contractible manner to bisect the sheet half 174. Above referenced U.S. Pat. Nos. 3,860,003 and 4,081,301 are incorporated herein by reference to show an elastic member secured to a diaper component in an elastically contractible manner.

The elastic member 154 can comprise two pieces of the above-referenced Findley Film. A first piece of film can have a free length of about 2.54 cm (inch) and can be stretched to a length of about 9.5 cm (3.75 inches) and applied to the center portion of the length of sheet half 174. The second piece of film can have a free length of about 9.5 cm (3.75 inches) and be stretched to a length of about 58 cm (23 inches) and applied to the length of the sheet half 174 to overlie the first piece of film. The two pieces of film comprising elastic member 154 contract the length of the sheet half 174 from a free length of about 61 cm (24 inches) to a contracted length of about 15.2 cm (6.0 inches).

The elastic member 161 can comprise a piece of the above-referenced Findley Film having a free length of about 1.9 cm (0.75 inch). The elastic member 161 is stretched to a length of about 7.6 cm (3 inches) and applied to the width of the sheet half 174 to contract the width from a free width of about 9.5 cm (3.75 inches) to a contracted width of about 5.1 cm (2.0 inches).

After securing the elastic members 154 and 161 to sheet half 174, sheet half 176 can be folded along a crease 178 (FIG. 3) to overlie sheet half 174 and the elastic members 154 and 161. Sheet half 176 can then be secured to sheet half 174 in any of several ways known in the art, such as by ultrasonic bonding, heat/pressure sealing, or by bonding the sheet halves 174 and 176 using adhesives or glues, such as an adhesive manufactured by the H.B. Fuller Company of St. Paul, Minn. under the name HL-1258, or a double sided adhesive tape such as 3M Tape No. 1524 available from The 3M Company of St. Paul, Minn. The resulting pocket cuff 50 comprises two layers formed by halves 176 and 174. However, two layers are not necessary to the operation of the pocket cuff 50, and a suitable pocket cuff 50 can be formed having just one layer, or having more than two layers.

The pocket cuff 50 formed in the manner described above is joined to an underlying element of diaper 20 along closed edge 52 to prevent leakage of body exudates past the rear waist region 24. The pocket cuff can be joined to topsheet 38 along closed edge 52, as shown in FIGS. 1 and 2. Alternatively, pocket cuff 50 can be joined to backsheet 42 along closed edge 52 if topsheet 38 does not extend fully into the rear waist region 24.

The pocket cuff 50 can be joined to an underlying element of diaper 20 along the closed edge 52 in any of several ways which are well known in the art. The pocket cuff 50 is preferably joined in a liquid tight relationship to the underlying element of diaper 20 along closed edge 52 such that body exudates are prevented from leaking between pocket cuff 50 and the underlying element of the diaper 20. For example, the pocket cuff 50 can be joined to the topsheet 38 with ultrasonic bonding, pressure/heat sealing, or with a continuous layer of an adhesive or glue, such as the HL-1258 adhesive or the 3M Tape No. 1524 referenced above.

The closed edge 52 can have a generally laterally oriented portion 180 extending between generally forward extending portions 182, as shown in FIG. 2. Closed edge 52 preferably extends rearward of the core edge 48 associated with rear waist region 24. Closed edge 52 also preferably extends laterally outward of core edges 46. The laterally extending portion 180 of closed edge 52 is spaced forward of end edge 32 in 35 rear waist region 24, and the forward extending portions 182 of closed edge 52 are spaced laterally inward from barrier cuffs 62 in the rear waist region 24, as shown in FIG. 2. Alternatively, the laterally extending portion 180 could coincide with the end edge 32 and the forward extending portions 182 could coincide with the proximal edges 64 of the barrier cuffs 62 in the rear waist region 24.

The open edge 54 or the pocket cuff 50 extends between the laterally spaced apart open edge ends 55. The open edge ends 55 are joined to the barrier cuffs 62 at a pair of laterally spaced apart junctures 155, as shown in FIGS. 1, 2, and 5. Each juncture 155 is positioned intermediate the first end 72 and the second end 74 of a barrier cuff 62.

FIG. 1 shows inflected barrier cuffs 62 having the distal edge 66 extending laterally inward of the proximal edge 64 at the first barrier cuff end 72, and the distal edge 66 extending laterally outward of the proximal edge 64 at the second barrier cuff end 74. FIGS. 6–9 illustrate the inflected nature of the barrier cuff 62. FIG. 6 is an instant sectional view taken along line 6—6 in FIG. 1, rearward of juncture 155. FIG. 6 shows the barrier cuff 62 "flipped out" with distal edge 66 of the barrier cuff 62 extending laterally outward of the proximal edge 64. FIGS. 8 and 9 are instant sectional views taken forward of the juncture 155. FIGS. 8 and 9 show the barrier cuff 62 "flipped in" in the crotch region 26, with the distal edge 66 of the barrier cuff 62 extending laterally inward of the proximal edge 64. Elastic members 77 space the distal edge 66 of the barrier cuff 62 above topsheet 38 to form channel 177. Channel 177 and the barrier cuff 62 contain body exudates and prevent leakage of the exudates from between the wearer's leg and the diaper 20.

Referring to FIGS. 1 and 7, each open edge end 55 can be joined to the distal edge 66 of a barrier cuff 62. In one preferred embodiment the elastic member 154 extends between the open edge ends 55. Each open edge end 55 is joined to a distal edge 66, such that the elastic member 154 is juxtaposed with the elastic members 77 operatively associated with the distal edges 66 of the barrier cuffs 62. The elastic members 77 can extend longitudinally rearward and laterally outward from each juncture 155 to underlie a portion of a tape tab fastener 82.

The open edge end 55 can be joined to the distal edge 66 of the barrier cuff 62 in any of several ways known in the art, such as by ultrasonic bonding, heat/pressure sealing, or by bonding using adhesives or glues, such as the HL-1258 adhesive or the 3M Tape No. 1524.

Referring to FIG. 7, a channel 171 can be formed between the closed edge 52 of the pocket cuff 50 and the proximal edge 64 of the barrier cuff 62 if the pocket cuff 50 is only joined locally to the distal edge 66 of the barrier cuff 62. Referring to FIG. 8, the pocket cuff 50 can be continuously joined along the full width W of barrier cuff 62 in order to close channel 171, thereby preventing longitudinal leakage of body exudates between the barrier cuff 62 and the pocket cuff 50.

The barrier cuff 62 is in a generally upright position at juncture 155, as shown in FIG. 7. The juncture 155 provides a transition, or inflection point, between the flipped out portion of barrier cuff 62 and the flipped in portion of the barrier cuff 62. The juncture 155 and the associated open edge end 55 also comprise the intersection of a generally Y-shaped load carrying structure.

Referring to FIG. 5, this Y-shaped load carrying structure comprises the open edge 54 of the pocket cuff 50 and also comprises the barrier cuff 62. A first branch 201 of the Y-shaped structure comprises a portion of barrier cuff 62 extending laterally outward and longitudinally rearward from an open edge end 55 to a tape tab fastener 82. This first branch 201 can include at least a portion of the distal edge 66 and elastic members 77.

The second branch 202 of the Y-shaped structure comprises a portion of the barrier cuff 62 extending longitudinally forward of open edge end 55. The second branch 202 can also extend laterally inward or laterally outward from the open edge 55. The second branch 202 can include at least a portion of the distal edge 66 and elastic members 77. In the preferred embodiment a single, continuous barrier cuff 62 comprises the first and second branches. However, in alternative embodiments the first and second branches can each comprise a separate barrier cuff structure.

The third branch 203 of the Y-shaped structure comprises a portion of the open edge 54. This third branch 203 can include a portion of the elastic element 154. In a preferred embodiment including a longitudinally oriented elastic member 161, the third branch 203 of the Y-shaped structure comprises portions of the open edge 54 and elastic element 154 which extend laterally inward and longitudinally rearward from an open edge end 55 to the apex 157.

The first branch 201 of the Y-shaped structure exerts a longitudinally rearward force component and a laterally outward force component on the open edge end 55. These force components are preferably transmitted from the tape tabs 82, shown in FIG. 1, as is discussed in more detail below. The longitudinally rearward force component biases the open edge end 55 away from the lateral centerline 34. The laterally outward force component biases the open edge end 55 away from the longitudinal centerline 36.

The two force components transmitted by the first branch 201 aid in shaping the open edge 54 of the pocket cuff 50 in the plane of the diaper 20. The plane of the diaper 20 is defined by the longitudinal and lateral centerlines 34 and 36. The two force components can also act to space the pocket cuff 50 apart from the topsheet 38, and thereby open pocket space 51 to receive body exudates.

The longitudinal force component in the second branch 202 of the Y-shaped structure offsets the longitudinal force component transmitted by the first branch 201 (as well as any longitudinal force component exerted on the open edge end 55 by the third branch 203). The second branch 202 of the Y-shaped structure exerts a longitudinally forward force which biases the open edge end 55 toward the lateral centerline 34. Each open edge end 55 can be viewed as being suspended between two series connected longitudinal springs. The elastic members 77 provide the spring compliance. The position of the open edge ends 55 is therefore variable with respect to the diaper end edge 32 in the rear waist region 24.

As the elastic members 77 in the distal edge 66 of the barrier cuff 62 are extended, such as when the diaper 20 is applied to the wearer, the position of the open edge ends 55 can shift longitudinally. The amount the elastic members 77 are extended will vary with the size of the wearer of the diaper 20. Therefore, the longitudinal position of the open edge ends 55 can advantageously vary to accommodate different size wearers.

The laterally inward force component exerted by the third branch 203 of the Y-shaped structure offsets the laterally outward force component exerted by the first branch 201. In particular, the open edge 54 acts as a structural connection between the two barrier cuffs 62. The lateral force component exerted by the open edge 54 helps to establish the point of inflection of the barrier cuffs 62, and helps to prevent the barrier cuffs 62 from becoming flipped out forward of the open end edges 55. It is desirable that the barrier cuffs 62 be maintained in a flipped in configuration forward of the open edge ends 55 to prevent leakage past the barrier cuffs 62 in the crotch region 26.

In order to establish the correct loading in the Y-shaped structure described above, the open edge ends 55 should be located intermediate the lateral centerline 34 and the fastening means 80. Preferably, the open edge ends 55 are positioned rearward of the lateral centerline 34 and forward of the forward most portions of the laterally spaced apart tape tabs 82. The open edge ends 55 should also be positioned laterally inward from the tape tabs 82.

For diaper embodiments fitting babies weighing between about 7.3 and 11.3 kg (16.0 and 25.0 lbs.), the open edge ends 55 should be laterally spaced apart about 8.9 to 11.4 cm (3.5 to 4.5 inches) when the diaper elastic is contracted. The open edge ends 55 should be positioned longitudinally forward from the diaper rear end edge 32 about 11.4 to 14.0 cm (4.5 to 5.5 inches) when the diaper elastic is contracted, and about 17.8 to 20.3 cm (7.0 to 8.0 inches) when the diaper is in its flat-out, uncontracted state (i.e., with all the elastic induced contraction in the barrier cuffs 62, the gasket cuffs 104, and wain elastic features 120 pulled out). The apex 157 should be positioned longitudinally forward of the diaper rear end edge 32 about 6.3 to 8.9 cm (2.5 to 3.5 inches) when the diaper elastic is contracted, and about 10.2 cm (4 inches) when the diaper is in its flat-out, uncontracted state. The included angle B formed by the open edge 54 at the apex 157 can preferably be between 45° and 135°. In one preferred embodiment the included angle B is less than 120° when the diaper elastic is contracted, and is less than 120° when the diaper 20 is in its flat-out, uncontracted state.

The distal edge 66 of each barrier cuff 62 can extend longitudinally rearward and laterally outward from an open edge end 55 to be operatively associated with a tape tab 82, shown in FIG. 1. The distal edge 66 can extend longitudinally rearward and laterally outward from an open edge end 55 to form an included angle A with the longitudinal centerline 34. This included angle A can be between about 10 to about 60 degrees when the diaper 20 is in its uncontracted state, as shown in FIG. 1.

The distal edge 66 of each barrier cuff 62 can be operatively associated with a tape tab 82 by directly or indirectly joining the distal edge 66 to a portion of the tape tab 82. Referring to FIG. 4, the distal edge 66 can be juxtaposed with a portion of the tape tab 82, and can be directly joined to a portion of the tape tab 82.

The tape tab 82 comprises a fixed portion 83 joined to the backsheet 42 and a tab portion 84 that is grasped by the diaperer when securing the diaper 20 to the wearer. The tape tab 82 also comprises a release portion 85 joined to the topsheet 38. The tab portion 84 includes an adhesive layer for attachment to a landing member (not shown) in the front waist region 22. During manufacture the tab portion 84 is folded to overlie the release portion 85 to protect the adhesive layer on tab portion 84. The release portion 85 may comprise silicone coated high density polyethylene. The release portion 85 allows the tab portion 84 to be extended without damaging the adhesive layer or the topsheet 38. U.S. Pat. No. 3,848,594 issued to Buell on Nov. 19, 1974, is incorporated herein by reference for the purpose of showing an exemplary tape tab construction. The tab portion 84 is shown folded in FIG. 4 and is shown extended for grasping in FIG. 2.

In the embodiment shown in FIG. 4, a portion of the release member 85 is juxtaposed over a portion of the distal edge 66. The release member 85 can be adhesively joined to a portion of the distal edge 66. The distal edge 66 can be juxtaposed over, and adhesively joined to, a portion of the rear waist region elastic feature 120. In FIG. 4, a portion of the distal edge 66 is juxtaposed with a portion of the elasticized side panel 126. A portion of the elasticized side panel 126, in turn, can be juxtaposed over, and adhesively joined to, the fixed portion 83 of the tape tab 82. Thus, a portion of the distal edge 66 and the elasticized side panel 126 are joined together and disposed between the release portion 85 and the fixed portion 83 of the tape tab 82.

Without being limited by theory, the distal edge 66 is juxtaposed with a portion of the tape tab 82 to provide a direct load path between the tape tab 82 and the juncture 155. The tape tab 82 is juxtaposed with a portion of the waist region elastic feature 120 to enhance the transfer of tape tab loads to the distal edge 66, and thus to juncture 155.

The diaper 20 is applied to the wearer by positioning the rear waist region 24 under the wearer's back and drawing the remainder of the diaper 20 between the wearer's legs, so that the front waist region 22 is positioned across the front of the wearer. The ends of the tape tabs 82 are then secured to the landing members (not shown) in the front waist region 22.

Figure 11:
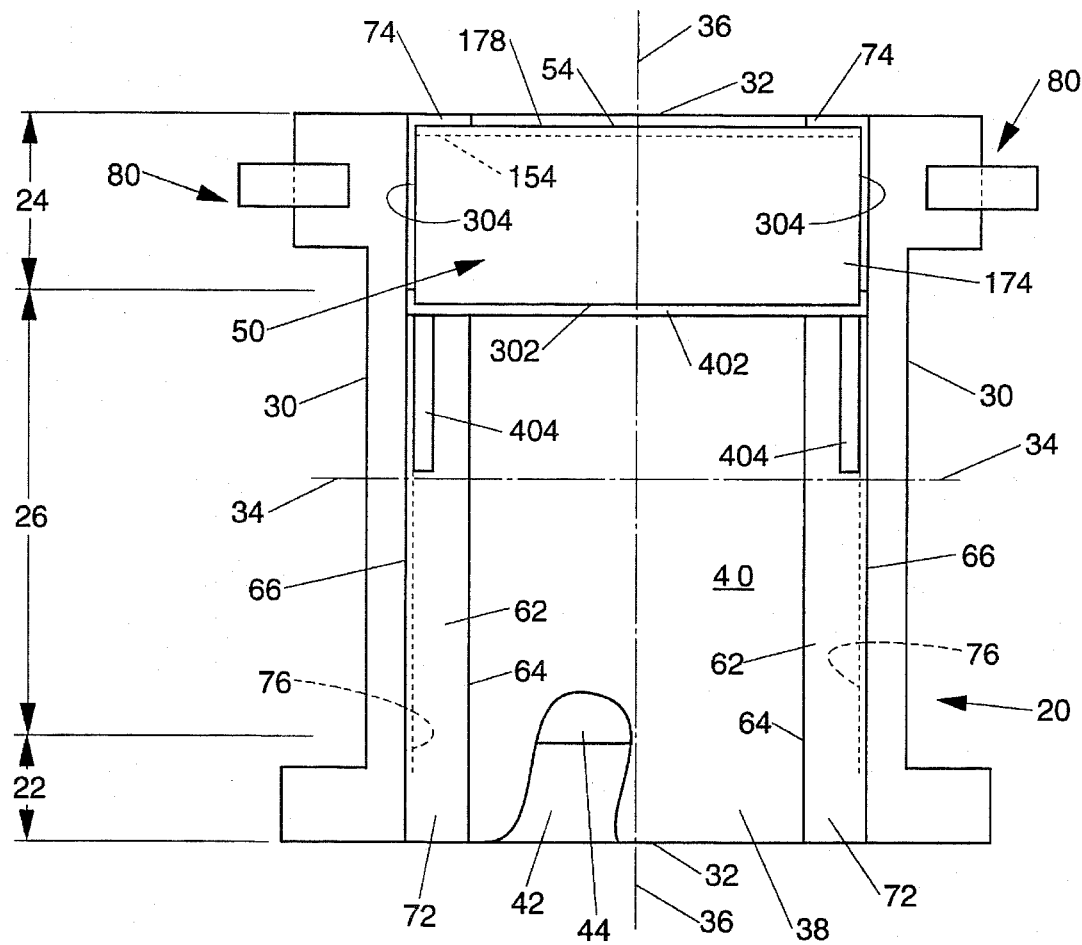
FIG. 11 is a top plan view of a partially constructed disposable diaper illustrating pocket cuff attachment to the diaper.
Figure 12:
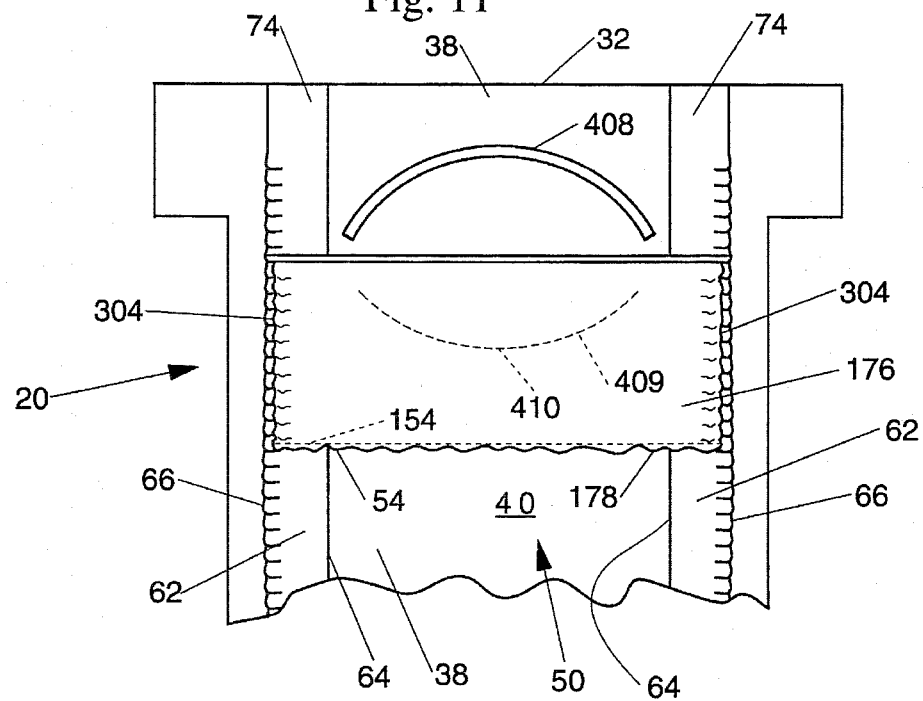
FIG. 12 is a top plan view of a partially constructed disposable diaper illustrating formation of an apex on the open edge of the pocket cuff wherein a portion of the pocket cuff substantially aligned with the longitudinal centerline of the disposable absorbent article is joined to an underlying portion of the disposable absorbent article to elastically extend the open edge of the pocket cuff and to position the apex longitudinally rearward of the open edge ends.

FIGS. 11-14 illustrate another embodiment of a disposable diaper 20 having a pocket cuff 50. FIGS. 11 and 12 illustrate steps in forming the completed diaper 20 shown in FIGS. 13 and 14. The diaper 20 shown in FIGS. 13-14 has barrier cuffs 62 which are not inflected, though it will be understood that the barrier cuffs 62 could be inflected if desired.

The pocket cuff 50 can be formed from a sheet of material, such as the above mentioned P-8 material. Such a material can have a stiffness in tension that varies with direction. The material is preferably oriented such that the direction of lowest stiffness of the material is aligned generally parallel to the longitudinal centerline 36.

The sheet of pocket cuff material can have a length of about ten inches and a width of about ten inches. An elastic member 154 having a free length of about four inches can be joined in an elastically contractible manner to extend widthwise along one side of the sheet of material midway along the length of the sheet. The elastic member 154 is elongated prior to it being joined to the sheet of pocket cuff material. The elongation of the elastic member 154 can vary with position along its length. For example, the free, relaxed elastic member 154 can have a total length of four inches with a one inch center portion, two adjacent 1.25 inch side portions, and two 0.25 inch end portions. In one embodiment, the center portion of the relaxed elastic member 154 can be elongated about 400 percent (to about four inches) prior to being joined to the sheet of material, the adjacent side portions can be elongated about 250 percent prior to being joined to the sheet of material, and the end portions can remain unelongated upon being joined to the sheet of pocket cuff material. A suitable elastic member 154 comprises Fulflex Ultraflex synthetic rubber manufactured by the Fulflex Company as Spec. No. 65325, 9EX29, 0.007× 5/64. The elastic element 154 can be joined to the sheet of material adhesively or by other means. A suitable adhesive for joining the elastic member 154 to the sheet of material is Findley Adhesive 2031 manufactured by Findley Adhesives.

Figure 14:
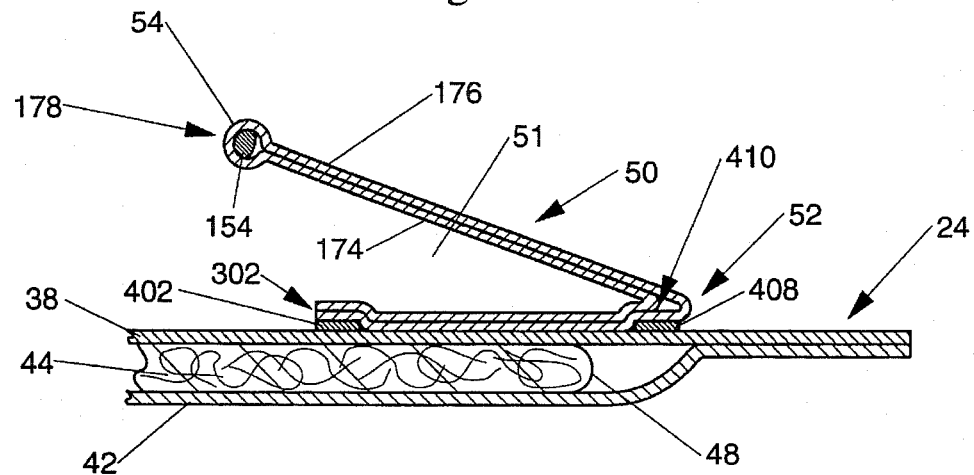
FIG. 14 is a fragmentary sectional view of the diaper of FIG. 13 taken along lines 14—14 in FIG. 13.

Once the elastic member 154 is joined to the sheet of pocket cuff material, the sheet of pocket cuff material is folded along a crease 178 corresponding to the pocket cuff open edge 54 (FIG. 14) to provide two sheet halves 174 and 176 (FIGS. 11, 12 and 14). The sheet halves 174 and 176 can be adhesively bonded together and trimmed to have a length parallel to the longitudinal centerline 36 of about four inches and a width parallel to the lateral centerline 34 of about 9 inches.

Referring to FIG. 11, the folded and trimmed pocket cuff sheet material can then be joined to an underlying portion of the disposable absorbent diaper 20. The folded and trimmed pocket cuff sheet material is joined to the diaper 20 with the distal edges 66 of the barrier cuffs 62 unattached to the underlying diaper structure and positioned laterally outward of the proximal edges 64 of the barrier cuffs 62. A laterally extending attachment means 402 joins an end 302 of the folded pocket sheet material to the topsheet 38 and the barrier cuffs 62. The attachment means 402 can be positioned about 5 inches longitudinally forward of the end edge 32 disposed in the rear waist region 24. Longitudinally extending pocket cuff side attachment means 404 are provided on each barrier cuff 62. The side attachment means 404 extend forward of the laterally extending attachment means 402.

Referring to FIG. 12, the crease 178 corresponding to the open edge 54 is brought forward of the end 302 so that pocket cuff side edges 304 can be joined to the barrier cuffs 62 by the side attachment means 404. The pocket cuff side edges 304 are joined to the barrier cuffs 62 while the elastic members 77 of the barrier cuffs are extended. When the forces holding the elastic members 77 in an extended state are released, the elastic members 77 elastically gather the pocket cuff side edges 304, as shown in FIG. 12. Each pocket cuff side edge 304 extends longitudinally rearward from the open edge 54, as shown in FIG. 12.

Figure 13:
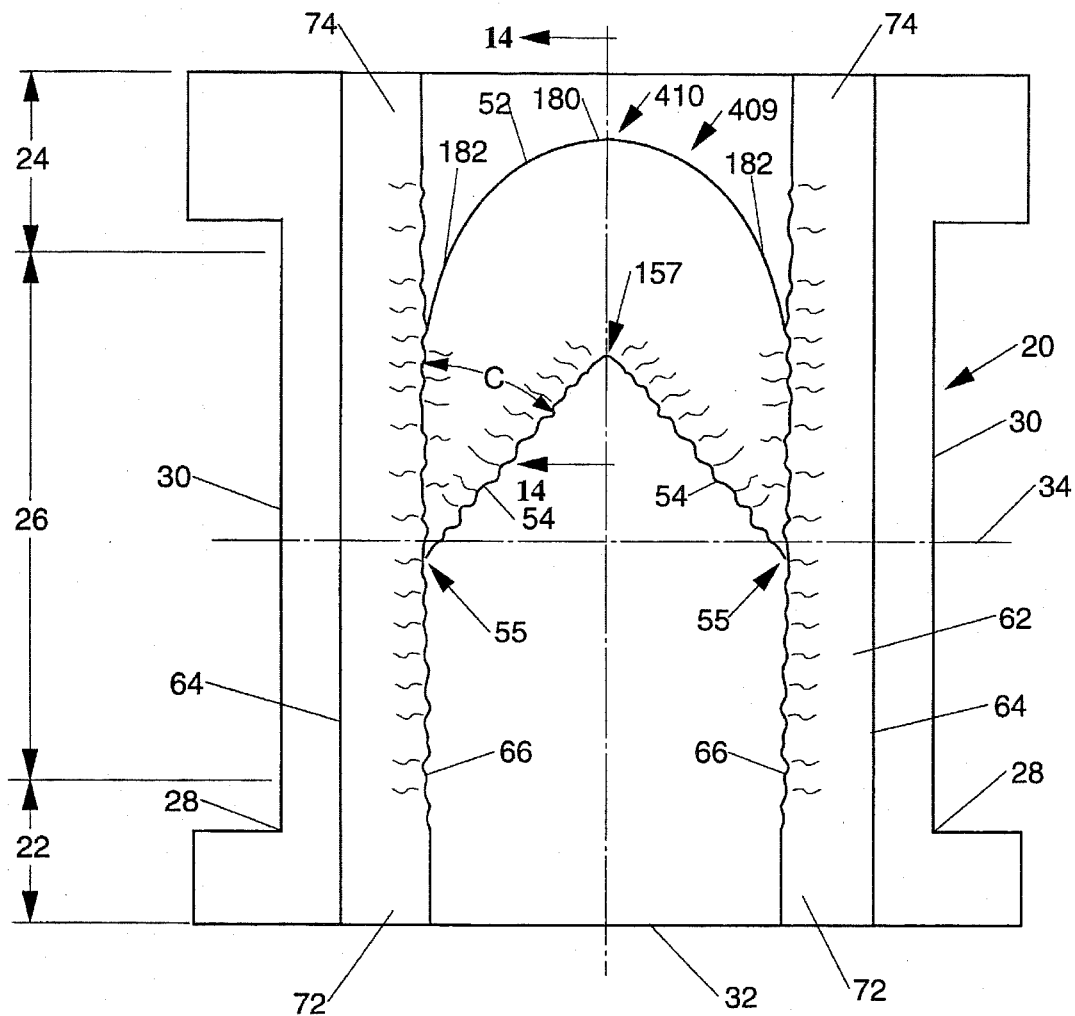
FIG. 13 is a top plan view of the completed disposable diaper of FIG. 12 showing the apex formed on the pocket cuff open edge.

Referring to FIGS. 12 and 13, the apex 157 is formed by joining a portion of the pocket cuff 50 substantially aligned with the longitudinal centerline 36 to an underlying portion of the diaper 20. In FIG. 12, a portion 409 of the pocket cuff 50, including a portion 410 substantially aligned with the longitudinal centerline 36 and disposed intermediate the open edge 54 and the end 302, is shown as an arcuate dotted line. The portion 410 of the pocket cuff 50 is displaced longitudinally rearward of the end 302 and joined to the topsheet 38 by an attachment means 408. Displacing the portion 410 of the pocket cuff 50 longitudinally rearward tensions the elastic element 154 and the portions of the elastic members 77 of the barrier cuffs 62 positioned forward of the open edge ends 55, thereby elastically extending the open edge 54 of the pocket cuff and positioning the apex 157 longitudinally rearward of the open edge ends 55. The pocket cuff open edge 54 is thereby elastically biased in the longitudinal direction by the elastic member 154 and the elastic members 77 to form the apex 157 (FIG. 13).

The portion 409 of the pocket cuff 50, when joined to the topsheet 38, provides a pocket cuff closed edge 52 (FIG. 13) comprising a central, generally laterally extending closed edge portion 180 disposed intermediate generally forwardly extending closed edge portions 182. The attachment means 408 can be shaped convex rearward, as shown in FIG. 12, to provide a convex rearward shaped closed edge 52, as shown in FIG. 13. Attachments means 402, 404, and 408 can comprise adhesive or other suitable attachment means. An example of suitable attachment means 402, 404, and 408 is ¼" double sided tape, No. 1524 manufactured by The 3M Company.

Once the side edges 304 and the closed edge 52 are formed, the distal edges 66 of the barrier cuffs 62 can be folded laterally inward of the proximal edges 64, as shown in FIG. 13. The distal edges 66 can then be adhesively secured to an underlying diaper structure laterally inward of the proximal edges 64 at the first and second barrier cuff ends 72 and 74.

In the embodiment shown in FIG. 13, the elastic members 77 in the distal edge 66 of the barrier cuffs 62 extend longitudinally rearward and longitudinally forward of the open edge ends 55. The open edge 54 extends longitudinally rearward and laterally inward of each open edge 55 to form an angle C with an adjacent distal edge 66 of a barrier cuff 62. The angle C can be between about 10 degrees and about 70 degrees when the diaper is in its flatout, uncontracted state. The apex 157 can be positioned longitudinally forward of the diaper rear end edge 32 from about 3 inches to about 5 inches when the diaper is in its flat-out, uncontracted state. The elastic members 77 and the elastic member 154 elastically gather the pocket cuff 50 and promote spacing of the open edge 54 from the topsheet 38

While particular embodiment of the present invention have been illustrated and described, it would be obvious to those skill in the art that various other changes and modifications can be made without departing from the spirit and scope of the present invention. It is therefore intended to cover in the appended claims all such changes and modifications.

What is claimed is:

1. A disposable absorbent article having a front waist region, a rear waist region longitudinally spaced from the front waist region, a crotch region disposed between the front and rear waist regions, longitudinal edges, end edges, a longitudinal centerline and a lateral centerline, the disposable absorbent article comprising:

a liquid pervious topsheet;

a liquid impervious backsheet joined to the topsheet;

an absorbent core positioned between the topsheet and the backsheet, the absorbent core having side edges and front and rear waist edges;

a side flap extending laterally outward from each side edge of the absorbent core;

a fastening means for securing the disposable absorbent article on the wearer;

a barrier cuff disposed adjacent each longitudinal edge of the disposable absorbent article, each barrier cuff extending longitudinally from a first barrier cuff end in the front waist region to a second barrier cuff end in the rear waist region, and each barrier cuff having a proximal edge and a distal edge, each proximal edge joined to a side flap, each barrier cuff being inflected to have the distal edge extending laterally inward of the proximal edge at the first barrier cuff end and the distal edge extending laterally outward of the proximal edge at the second barrier cuff end;

spacing means operatively associated with each barrier cuff for spacing a portion of each barrier cuff distal edge apart from the topsheet; and a pocket cuff positioned intermediate the barrier cuffs and operatively associated with the fastening means, the pocket cuff having an open edge extending intermediate the inflected barrier cuffs.

2. The disposable absorbent article of claim 1 wherein the open edge end extends intermediate laterally spaced apart open edge ends, and wherein each open edge end is joined to a barrier cuff at a juncture positioned intermediate the first and second barrier cuff ends.

3. The disposable absorbent article of claim 2 wherein the open edge has an apex positioned intermediate the open edge ends, the apex disposed longitudinally rearward of a line passing through the open edge ends.

4. The disposable absorbent article of claim 3 wherein the apex is positioned substantially on the longitudinal centerline of the disposable absorbent article.

5. The disposable absorbent article of claim 3 wherein the apex is positioned substantially equidistant from the open edge ends.

6. The disposable absorbent article recited in claim 1 wherein the pocket cuff is elastically extensible intermediate the pocket cuff open edge ends.

7. The disposable absorbent article recited in claim 6 wherein the pocket cuff open edge is elastically extensible intermediate the apex and each of the pocket cuff open edge ends.

8. The disposable absorbent article recited in claim 7 wherein the pocket cuff open edge comprises an elastic member extending intermediate the open edge ends.

9. The disposable absorbent article recited in claim 3 wherein a portion of the pocket cuff is joined to an underlying portion of the disposable absorbent article to elastically extend the open edge of the pocket cuff and to position the apex longitudinally rearward of the open edge ends.

10. The disposable absorbent article recited in claim 3 wherein a distal edge of a barrier cuff extends longitudinally rearward and laterally outward from each juncture.

11. The disposable absorbent article recited in claim 10 wherein said fastening means comprises a pair of fastening members, and wherein the distal edge of a barrier cuff extends intermediate a juncture and a fastening member.

12. The disposable absorbent article recited in claim 3 comprising an elastic member for biasing each pocket cuff open edge end longitudinally rearward and laterally outward.

13. The disposable absorbent article recited in claim 12 further comprising an elastic member for biasing each pocket cuff open edge end longitudinally rearward and laterally inward.

14. The disposable absorbent article recited in claim 13 further comprising an elastic member for biasing the pocket cuff open edge apex longitudinally rearward.

* * * * *

UNITED STATES PATENT AND TRADEMARK OFFICE
CERTIFICATE OF CORRECTION

PATENT NO. : 5,531,730
DATED : July 2, 1996
INVENTOR(S) : Kimberly A. Dreier

It is certified that error appears in the above-indentified patent and that said Letters Patent is hereby corrected as shown below:

Column 11, line 56     between "(" and "inch" insert --1--..
Column 12, line 49     delete "35".
Column 15, line 6      delete "wain" and insert --waist--.

Signed and Sealed this

Twenty-seventh Day of May, 1997

Attest:

BRUCE LEHMAN

*Attesting Officer*     *Commissioner of Patents and Trademarks*